United States Patent [19]

Worthrich

[11] Patent Number: 4,898,162
[45] Date of Patent: Feb. 6, 1990

[54] CONVERTIBLE EYESHIELD

[75] Inventor: Theodore S. Worthrich, Long Beach, Calif.

[73] Assignee: Surgin Surgical Instrumentation, Inc., Placentia, Calif.

[21] Appl. No.: 247,841

[22] Filed: Sep. 22, 1988

[51] Int. Cl.$^4$ ............................................. A61F 13/00
[52] U.S. Cl. ................................... 128/155; 128/163; 128/888; 128/894; 2/15; 604/332; 604/345
[58] Field of Search ...................... 2/15, 440; 128/163, 128/857, 858, 889, 890, 893, 894; 604/332, 345

[56] References Cited

U.S. PATENT DOCUMENTS

| | | |
|---|---|---|
| 591,244 | 10/1897 | Wylie . |
| 1,161,321 | 11/1915 | Lush . |
| 2,389,223 | 2/1941 | Werner ........................................ 2/15 |
| 2,543,104 | 2/1951 | Golding . |
| 3,022,786 | 2/1962 | Nalon ................................... 604/345 |
| 3,339,206 | 9/1967 | Daley . |
| 3,952,735 | 4/1976 | Wirtschafter et al. . |
| 4,303,063 | 12/1981 | Stahl . |
| 4,473,370 | 9/1984 | Weiss . |
| 4,677,974 | 7/1987 | Leonardi ............................. 128/163 |
| 4,701,962 | 10/1987 | Simon .................................. 128/858 |
| 4,727,869 | 3/1988 | Leonardi ............................. 128/163 |

Primary Examiner—Richard J. Apley
Assistant Examiner—N. Paul
Attorney, Agent, or Firm—Merchant & Gould

[57] ABSTRACT

An eyeshield which can be attached either by tape or a removable band over the eyesocket of a patient after surgery is of low friction resilient material and includes integral low profile bosses that are spaced apart near diametrically opposed edges. A flexible band having snap fasteners adjacent each end may be attached to the bosses on the eyeshield. The band having snap fasteners is easily released from the eyeshield by gripping extending fringes of the end portions of the band.

4 Claims, 3 Drawing Sheets

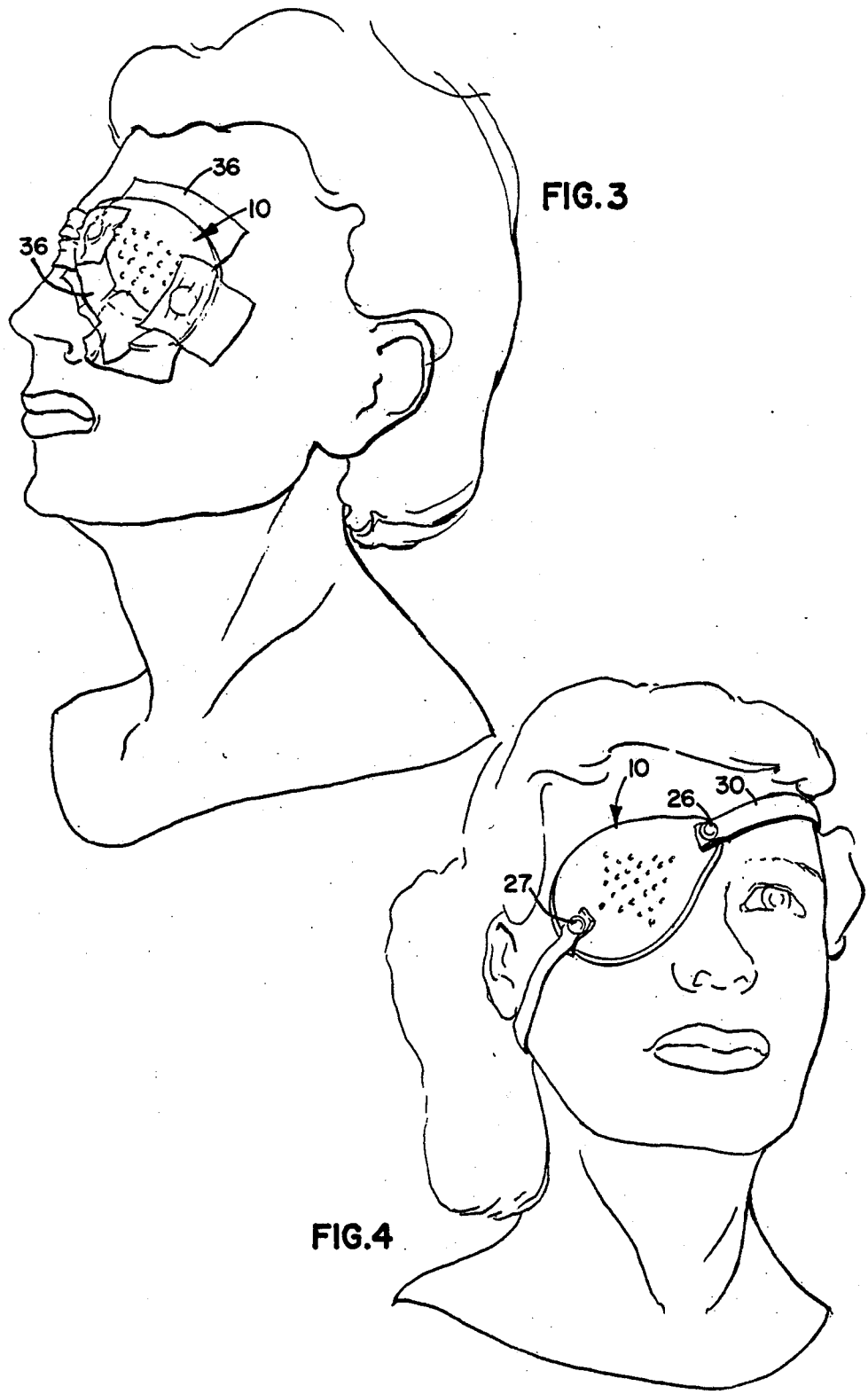

CONVERTIBLE EYESHIELD

BACKGROUND OF THE INVENTION

This invention relates to eyeshields for protecting the human eye, and particularly to an eyeshield capable of use in different modes in the post-operative phase.

Eyeshields have traditionally been used as protective barriers following eye surgery. Eyeshields reduce the chance of trauma to the eye or the orbital region and help protect against gross contamination.

Following eye surgery, such as a cataract operation, the eye must be protected from all external contact for a period of time. Thus, the surgeon usually immediately covers the eye with a shield that is taped into place. Subsequently, when the patient returns for the first post-operative examination, the surgeon removes the tape and the eyeshield. If the healing process is progressing satisfactorily, an eyeshield is thereafter typically used only under circumstances in which accidental contact might occur, as when sleeping. The application of the eyeshield during this recovery phase has traditionally either been by the patient taping an eyeshield in place over the eye or by using removable and replaceable eyeshields having permanently attached bands which fit around the back of the head. Thus, two different attachment means have been used (taped on or held in place by a band), and as far as is known, separate eyeshield units have always been employed for these applications. Repeated taping of an eyeshield in place results in irritation, although the taped in place unit must be used when immobilization must be assured. Thus, when only a temporary eye protector is needed, particularly on a repetitive basis, a band-attached system can be much more quickly and conveniently applied. Illustrative of this approach are the patents to Lush, U.S. Pat. No. 1,161,321, and Leonardi, U.S. Pat. No. 4,677,974. Some utilize a pad for direct contact with the eye, under the shield, as shown by the Leonardi Patent. In others, such as Wylie, U.S. Pat. No. 591,244, Werner, U.S. Pat. No. 2,389,223 and the Lush Patent, there is no contact.

A number of problems are presented to those who seek to provide an easily attached and replaceable eyeshield capable of use in different post-operative phases. The aged and infirm, who have limited manual dexterity, represent a substantial fraction of the population requiring eye surgery. Attachment of an eyeshield, whether by tape or by band, should be effected without undue difficulty by such persons. Each means by which the eyeshield is held in place should not conflict with the alternative mode of attachment or present undue danger to the patient. There should be no projections or contours that interfere either with the tape attachment or preclude easy fastening over the eye area.

SUMMARY OF THE INVENTION

In accordance with the invention, a concave-convex eyeshield is provided having an outline that includes a generally circular portion and a projecting sidelobe portion, and also includes low profile bosses at diametrically opposed regions adjacent the edges of the circular portion and the lobe portion. The bosses have central female recesses or sockets for receiving the male member in a snap-type fastener at one end of an elastic band, and slightly converging sides extending away from the base. The eyeshield body is of a low friction, resilient and shock absorbing plastic having a rounded peripheral edge. With this arrangement, the eyeshield can be taped in place during the immediate post-operative phase, with the tape spanning the edges of the shield to hold it in position. Thereafter, the tape can be readily removed and the elastic band can be affixed by engaging the snaps into the bosses, with the band extending around the back of the head to hold the eyeshield in place. The low profile bosses do not protrude to an extent which endangers the protected eye if contact is made, or inhibit the placing of tape over them. When the snap fasteners are used to attach the band, extending fringes on the ends adjacent the snaps can be gripped by the user, who can then separate the band from the eyeshield without difficulty, even without full control of the fingers. The eyeshield protects the eye from contact and trauma following eye surgery, such as cataract surgery or corneal abrasion. Sterile pads can be placed under the eyeshield if desired to assure immobilization.

BRIEF DESCRIPTION OF THE DRAWINGS

Better understanding of the invention may be had by reference to the following description, in conjunction with the accompanying drawings, in which:

FIG. 3 is a perspective view of the eyeshield of FIGS. 1 and 2 as attached by a band to a patient in the immediate post operative phase, and FIG. 4 is a different perspective view showing the eyeshield of FIGS. 1 and 2 used in conjunction with a band in the replaceable mode.

DETAILED DESCRIPTION OF THE INVENTION

Figure 1:
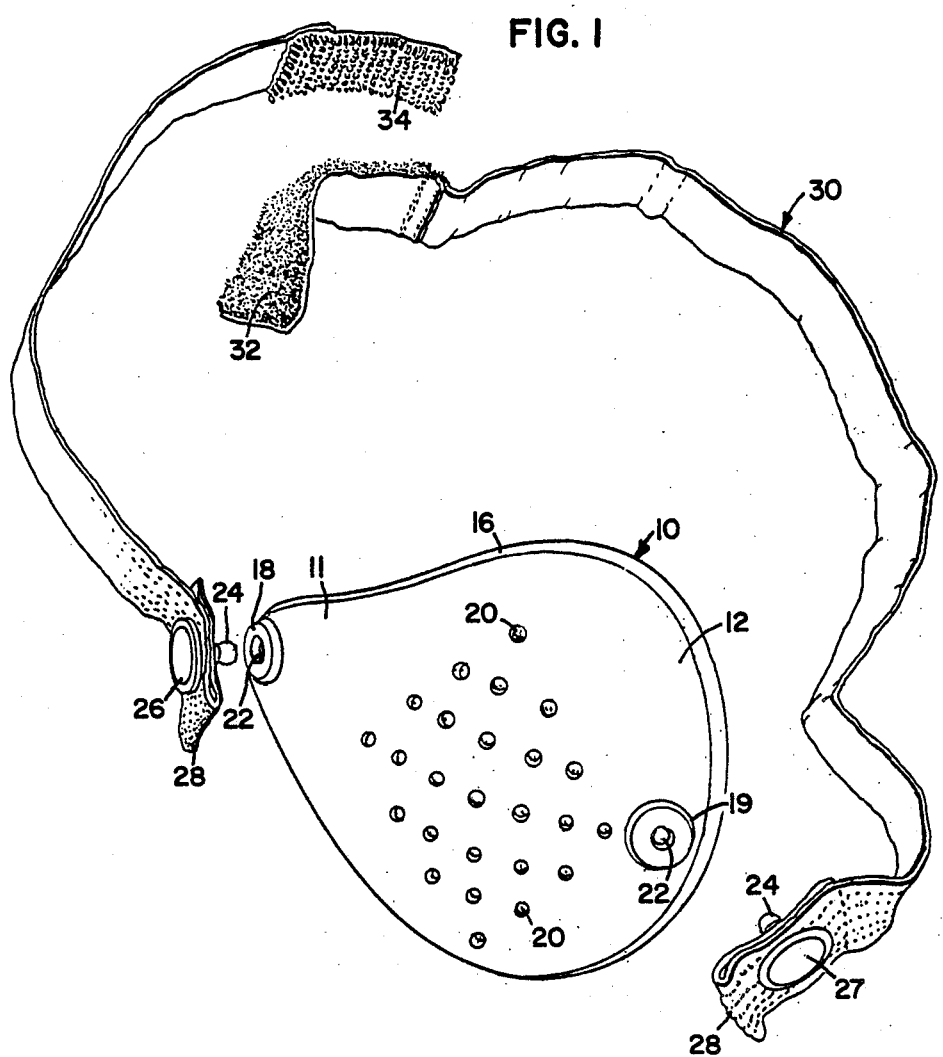
FIG. 1 is perspective view in exploded form of the principal elements of a convertible eyeshield in accordance of the invention.
Figure 2:
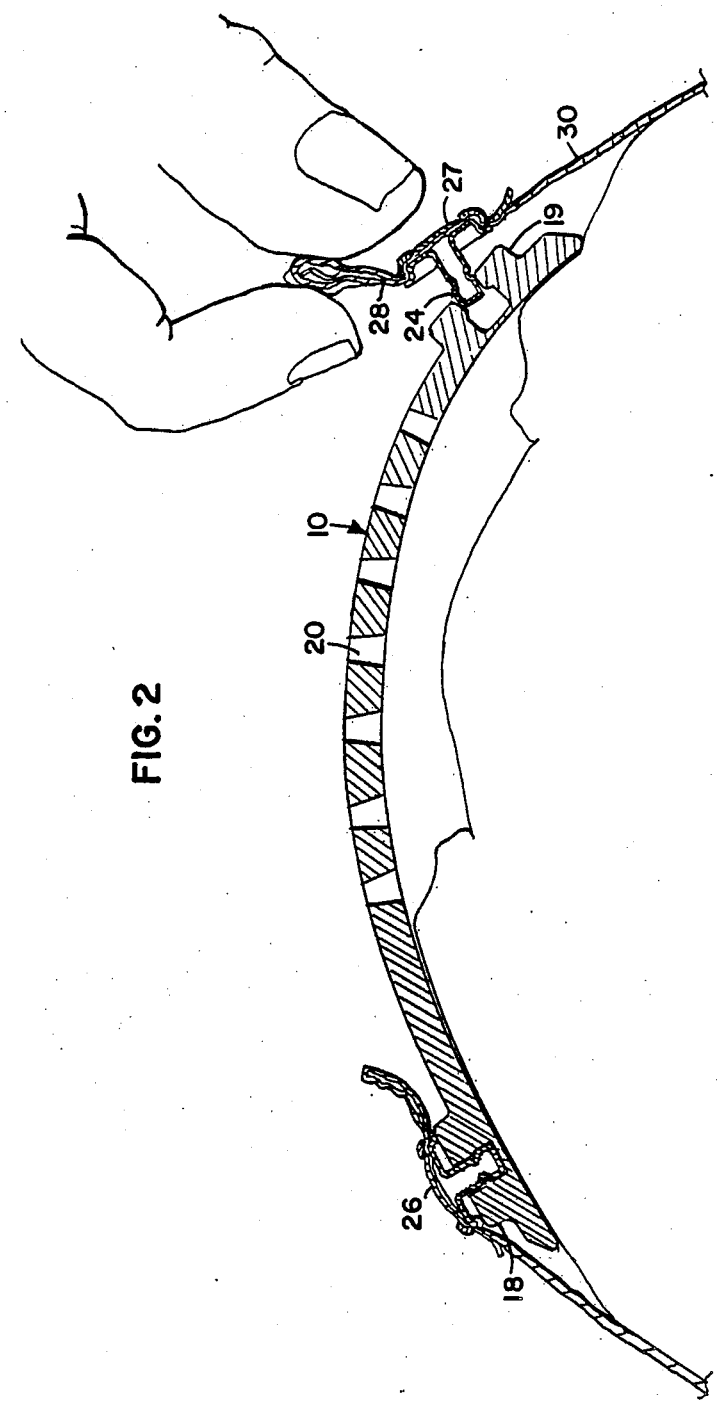
FIG. 2 is a cross-sectional view of the eyeshield of FIG. 1.

An eyeshield device in accordance with the invention, referring now to FIGS. 1 and 2, comprises a concave-convex eyeshield body 10 having a peripheral outline defined by a generally circular portion and an extended lobe portion 12 on one side. The lobe 12 outline commences at edges tangential to the circular portion, the lobe 12 continuing the concave-convex curvature. The body 10 is of high strength engineering plastic such as "Nylon∞ or "Teflon." Such materials have a low friction surface and are mechanically strong but resilient. Alternatively, the eyeshield device can be made from a suitable metal, such as aluminum, instead of a high strength plastic. A rounded peripheral edge surface 16 on the eyeshield 10 permits comfortable fit against the contacted surfaces of the orbital bone structure defining the eyesocket, and prevents sharp penetration of the surface of the skin in the event of impact or pressure on the eyeshield 10. An eyeshield edge protector of a soft elastic or cotton material can optionally be placed around the perimeter of the eyeshield to further enhance comfort during use of the eyeshield 10, to reduce irritation to the skin and to absorb perspiration. A pair of bosses, 18, 19, are integrally formed in the convex surface of the eyeshield 10 at one position near the tip edge of the lobe 11 and at a diametrically opposed region close to the edge of the circular portion 12, respectively. Perforations 20 can be placed within the central region of the eyeshield body 10 to permit air circulation and allow light to pass, but these are optional.

The bosses 18, 19, as seen particularly in FIG. 2, have low profiles, being between about one-quarter inch to three sixteenths of an inch in height, with each boss including a central recess or socket 22 for receiving the male member 24 on a snap fastener 26 or 27. The snap fasteners 26, 27 are separately attached to folded end portions 28 of a flexible band 30, which is formed of two sections. One section of the band 30 has a terminal strip of hook material 32 and the other has a strip of loop material 34, forming an attachment means of the commonly known "Velcro" type. Thus, the band 30 can be separated and readjusted in the mid region, if desired. The doubled over end portions 28 of the band 30 overhang the snap fastener 26, 27 elements so that, as seen in FIG. 2, either end can be gripped with the fingers to remove the snap fastener 26 or 27 from the adjacent boss 18 or 19. The low friction material of the boss 18 or 19 and the extended fringes of the doubled over ends 28 of the band 30 enable separation of the boss 18 or 19 and the snap fastener 26 or 27 without difficulty despite limited dexterity in the individual. The sides of the bosses 18, 19 include converging tapers in a direction away from the eyeshield body 10, which further facilitates gripping of the end portions 28.

Generally, following surgery to the eye, the doctor will tape a sterile cotton oval eye pad in place to ensure immobilization of the anesthetized eye. As seen in FIG. 3, in the immediate post-operative phase, the doctor then places the eyeshield 10 over the eye and sterile cotton eye pad, and attaches the eyeshield 10 over the eye with tape strips 36 across the edges, usually covering the low profile bosses 18, 19. Placing the tape strips 36 over the entire eyeshield 10 is not necessary inasmuch as the tape strips 36 need only bridge across the edges of the eyeshield 10 to hold the eyeshield 10 in place. The eyeshield 10 is universal in style, in that it will fit over either the left or the right eye. Following an adequate post-recovery period with the eyeshield 10 in place, typically 24 to 48 hours, the surgeon removes the cotton eye pad, the tape strips 36 and the eyeshield 10 for a post-operative examination. If the healing process appears to be progressing satisfactorily, the eyeshield 10 need be worn as a protective device for approximately two to four weeks only when there is a danger of external contact with the eye or when activities are performed where eye trauma is a concern, as when sleeping or engaging in exercise. This insures against any inadvertent contact with the eye. For this, the band 30 is attached to the eyeshield 10 by affixing the snaps 26, 27 into the bosses 18, 19, and looping the band 30 about the back of the head, as seen in FIG. 4. For adjustment of length or separately for removal of the eyeshield 10, the Velcro attachment 32, 34 can be taken apart or repositioned. Using the eyeshield 10 with the band 30 attached is beneficial to the patient since use of the band eliminates the skin irritation and inflammation which results from the continuous removal and reapplication of adhesive tape when an eyeshield is taped onto the patient's skin.

Perforations 20 on the eyeshield 10 can be used or not, and in different patterns as desired. The size of the eyeshield 10 can be selected in accordance with the requirements of an individual patient. The curvature of the surfaces can also be varied, as can the exterior shape. However, the shape shown with a lobe extending from one side in a circular geometry is the shape typically used.

The doctor and the patient have the option of attaching the eyeshield 10 with tape strips with the band 30 removed, or, alternatively, with the band 30 attached without the use of tape. Since the eyeshield 10 can be used in either form, only one eyeshield is required. The use of the eyeshield 10 with the band 30 attached eliminates the difficulty of retaping an eyeshield to the patient's face, which is particularly important to elderly patients whose manual dexterity may be a severe problem. The patient need not fumble with tape and scissors since the band 30 with the snaps 26, 27 can be easily attached to or removed from the eyeshield 10 by the patient. In addition, when the flexible band 30 is utilized, irritation of the patient's skin due to application and removal of adhesive tape is eliminated.

While various forms and modifications in accordance with the invention have been suggested, it will be appreciated that the invention is not limited thereto but encompasses all expedients within the scope of the appended claims.

I claim:

1. An eyeshield which can be taped over an eyesocket of a person by a health professional or a patient or alternatively, applied repeatedly without the use of tape by the patient himself, said eyeshield covering an eye and preventing any contact with the eye, thereby protecting the eye following an injury or surgery, comprising:

(a) a low friction, yieldable, light weight, high strength, self-supporting, eyeshield body having a first and a second surface, the first surface being a convex outer surface, the second surface being an inner concave surface, the eyeshield body having rounded edges and an outline fitting against the orbital bone structure of a face in fixed, non-contacting relation over the eye and including a periphery defining a generally circular portion and an extension therefrom;

(b) a pair of socket bosses not greater than one quarter inch in height integral with the convex surface of the eyeshield body adjacent the edge of the extension thereon on a first end and adjacent the edge of the circular portion on a second end, said bosses allowing the eyeshield to be taped onto the face of the person over the eyesocket; and (c) releasable means for holding the eyeshield body over the eyesocket, said releasable means comprising an elastic band for encircling the head of the person over the eyebrow on one side of a face and under the ear lobe on the other side of the face, the band comprising a pair of sections having first and second interengaging fastening members on the ends opposite the snap fastener end, said interengaging fastening members comprising intercoupling hook and loop sections.

2. The invention as set forth in claim 1 above, wherein the band comprises male snap fastener means adjacent each end thereof, and wherein the band includes terminal portions protruding past the snap fastener means which may be gripped by the person for release of the band from the eyeshield.

3. The invention as set forth in claim 2 above, wherein the snap fastener means each comprise a male member registrable in the socket of a different boss, and wherein the bosses are of about 3/16 inch or less in height and have converging sides in a direction away from the eyeshield body.

4. An eyeshield device for use with tape or band attachment comprising:
(a) a high strength eyeshield body having a shape which has a first and second surface, the first surface being a convex outer surface and the second surface being an inner concave surface and including a pair of spaced- apart bosses on the convex surface thereof, the body being of low friction material and the bosses being integral within and including sockets therein; and,
(b) removable band means having fastener elements adjacent each end thereof, the fastener elements being receivable in the sockets in the bosses, such that the eyeshield device can be taped over the eye with the band means removed or held in place by the band means encircling the head.

* * * * *

UNITED STATES PATENT AND TRADEMARK OFFICE
CERTIFICATE OF CORRECTION

PATENT NO. : 4,898,162

DATED : February 6, 1990

INVENTOR(S) : Theodore S. Wortrich

It is certified that error appears in the above-identified patent and that said Letters Patent is hereby corrected as shown below:

Title page:
"[75] Inventor: Theodore S. Worthrich" should read --[75] Inventor: Theodore S. Wortrich--. Column 2, line 46, "Nylonoo" should read --"Nylon"--. Column 6, line 1, after "integral", "within" should read --therewith--.

Signed and Sealed this

Twenty-ninth Day of September, 1992

Attest:

DOUGLAS B. COMER

*Attesting Officer*   *Acting Commissioner of Patents and Trademarks*